(12) United States Patent
Von Rüden et al.

(10) Patent No.: US 12,099,018 B2
(45) Date of Patent: Sep. 24, 2024

(54) INSPECTION APPARARATUS FOR THE INSPECTION OF CYLINDRICAL METAL FORMED PARTS

(71) Applicant: H&T Marsberg GmbH & Co. KG, Marsberg (DE)

(72) Inventors: Gregor Von Rüden, Marsberg-Oesdorf (DE); Martin Kinold, Marsberg-Giershagen (DE); Tobias Götte, Marsberg (DE); Daniel Rosenkranz, Marsberg-Oesdorf (DE)

(73) Assignee: H&T Marsberg GmbH & Co. KG, Marsberg (DE)

( * ) Notice: Subject to any disclaimer, the term of this patent is extended or adjusted under 35 U.S.C. 154(b) by 321 days.

(21) Appl. No.: 17/736,771

(22) Filed: May 4, 2022

(65) Prior Publication Data

US 2022/0357282 A1 Nov. 10, 2022

(30) Foreign Application Priority Data

May 4, 2021 (DE) ..................... 10 2021 111 517.5

(51) Int. Cl.
*G01N 21/90* (2006.01)
*G01N 21/88* (2006.01)
*G01N 33/20* (2019.01)
*G01N 21/84* (2006.01)

(52) U.S. Cl.
CPC .......... *G01N 21/90* (2013.01); *G01N 21/8851* (2013.01); *G01N 33/20* (2013.01); *G01N 2021/845* (2013.01)

(58) Field of Classification Search
CPC .... G01N 21/90; G01N 21/8851; G01N 33/20; G01N 2021/845
See application file for complete search history.

(56) References Cited

U.S. PATENT DOCUMENTS 6,959,108 B1 * 10/2005 Bartelt ................. G01N 21/952
850/10

* cited by examiner

*Primary Examiner* — Jamil Ahmed
(74) *Attorney, Agent, or Firm* — MARSHALL, GERSTEIN & BORUN LLP

(57) ABSTRACT

An Inspection apparatus (9) for inspecting cylindrical metal formed parts comprises a guide (11) for guiding the metal formed parts to be inspected through the inspection apparatus (9). The inspection apparatus (9) further comprises a radiation device which is adapted to emit radiation in the direction of the guided metal formed parts, so that the radiation impinges on each of the metal formed parts and is at least partially reflected therefrom as reflection radiation. A sensor device of the inspection apparatus is adapted to receive the reflection radiation and convert it into image data. An evaluation device is designed to assess, based on an evaluation of the image data, whether the respective metal formed part has production-related defects.

18 Claims, 3 Drawing Sheets

INSPECTION APPARARATUS FOR THE INSPECTION OF CYLINDRICAL METAL FORMED PARTS

CROSS-REFERENCED TO RELATED APPLICATIONS

The benefit of priority to German Patent Application No. 10 2021 111 517.5 filed May 4, 2021, is hereby claimed and the disclosure is incorporated herein by reference in its entirety.

TECHNICAL FIELD

The present invention relates to an inspection apparatus for inspecting cylindrical metal formed parts.

BACKGROUND OF THE INVENTION

Cylindrical metal formed parts such as battery cups or aerosol containers for metered dose inhalers are typically produced by deep drawing. For this purpose, a blank is punched out of a metal sheet, drawn to form a cup and then deep-drawn in multiple deep-drawing steps by means of a punch and a die into a metal formed part, in particular into a battery cup or an aerosol container.

If, for example, the metal sheet has production-related slag inclusions, these slag inclusions can lead to surface defects, for example parabolic cracks, holes or similar drawing defects, in the deep-drawn metal formed part. In addition, impurities, for example metal chips, in the die can also lead to surface defects, in particular holes, in the metal formed parts. It is therefore necessary to inspect the metal formed parts for manufacturing-related defects after they have been produced. This inspection is currently carried out manually. An employee randomly checks individual metal formed parts for defects. If individual metal formed parts show defects, the entire batch has to be inspected. This leads to increased costs, as the follow-up inspection of entire production batches in particular is carried out externally by service providers.

Prior art inspection apparatuses are known which are used as part of a production line to monitor the quality of the manufactured products.

DE 10 2004 052 508 A1 relates to a system for measuring a body and monitoring the surface of the body using a camera device. The system is used for checking endless profiles by means of electronic digital image processing. Irradiation of the profile surface by means of a suitable light source and detection of the reflected radiation by an electronic camera device with subsequent electronic image processing allows conclusions to be drawn about the dimensions and tolerances of a body as well as about the quality of its surface.

For a continuously reliable quality control of the produced metal formed parts, it is necessary that they are passed in an approximately constant position relative to the inspection apparatus, for example the camera device. This can be realized without further ado in the case of endless profiles. However, in the case of individual smaller products, such as battery cups or aerosol containers, especially at high cycle rates of up to 400 metal formed parts per minute, this has not been possible up to now.

It is therefore the object of the present invention to provide an inspection apparatus for inspecting cylindrical metal formed parts, which enables inspection of individual metal formed parts at high cycle rates.

SUMMARY OF THE INVENTION

The object is solved by an inspection apparatus comprising the features of claim 1. Preferred embodiments are set out in the dependent claims.

According to the present invention, the inspection apparatus comprises a guide for guiding the metal formed parts to be inspected through the inspection apparatus. The inspection apparatus further comprises a radiation device adapted to emit radiation in the direction of the guided metal formed parts, so that the radiation impinges on each of the metal formed parts and is at least partially reflected therefrom as reflection radiation. Preferably, the radiation device is formed as light sources and the emitted radiation is light with a wavelength in the range from 400 nm to 800 nm.

The inspection apparatus further comprises a sensor device that is adapted to receive the reflection radiation and convert it into image data. Optionally, the sensor device is a camera device. Furthermore, an evaluation device is part of the inspection apparatus according to the invention. The evaluation device is designed to assess, based on an evaluation of the image data, whether the respective metal formed part has production-related defects. Optionally, the image evaluation is computer-aided by means of appropriate software.

According to the invention, the guide is formed by a guide tube. The guide tube is configured to receive the metal formed parts to be inspected so that they are guided in the guide tube through the inspection apparatus. The guide tube has a transmittance for the radiation of 80% to 95%, measured at a wall thickness of the guide tube of 2 mm and for radiation from a wavelength range of 400 nm to 800 nm. The guide tube has an average coefficient of linear thermal expansion according to ISO 7991 of at most $5 \times 10^{-6}$/K. Preferably, the guide tube has a refractive index of 1.4 to 1.5, in particular 1.473.

The use of a guide tube makes it possible to guide individual small metal formed parts, for example with the dimensions of a battery cup, through the inspection apparatus automatically, i.e. without manual working steps. This ensures that the metal formed parts are always moved past in the same position relative to the radiation device and the sensor device. Production-related defects can thus be reliably detected. In addition, a transmittance of the guide tube of between 80% and 95% enables the radiation emitted by the radiation device to pass through the guide tube and impinge on the metal formed parts to be inspected. Said transmittance further allows the radiation reflected from the metal formed parts to be inspected to pass through the guide tube again and impinge the sensor device. The average linear thermal expansion coefficient of at most $5 \cdot 10^{-6}$/K results in temperature stability, so that any heating of the guide tube caused by the radiation device causes negligible damage or deformation of the guide tube. As a result, reflection of the radiation on the metal formed parts is, if at all, only negatively affected in a negligible way.

According to an embodiment of the invention, the guide tube has a transmittance of 80% to 95%, measured even at a wall thickness of the guide tube of 4 mm and for radiation from a wavelength range of 400 nm to 800 nm.

According to another embodiment of the invention, the guide tube has a Knoop's hardness $HK_{0.1/20}$ according to ISO 9385 of 200 to 700. The hardness of the guide tube prevents the metal formed parts from damaging the surface of the guide tube, for example in the form of grooves, scratches or through abrasion, and thereby clouding it. The hardness of the guide tube thus ensures that the claimed transmittance of 80% to 95% is maintained during use of the guide tube and is not reduced by damage from the metal formed parts.

Preferably, the guide tube is made of borosilicate glass. Borosilicate glass is particularly robust, impact-resistant and cut-resistant. It is heat-resistant and can therefore be used at high temperatures. It withstands strong temperature fluctuations and also has a high chemical resistance.

According to a further embodiment, the borosilicate glass is an alkaline-earth free borosilicate glass. Alkaline-earth free borosilicate glass is also called borosilicate glass 3.3. Preferably, borosilicate glass 3.3 with the designation Duran® from the company Schott AG, 55122 Mainz, Germany, is used for the guide tube. Borosilicate glass 3.3 conforms to DIN ISO 3585, is highly resistant to chemicals, has very good thermal shock resistance and can therefore be used for a wide range of applications, for example in glass device construction, laboratory articles and for arts and crafts purposes. Duran® has sufficient resistance for continuous transport of metal formed parts. The metal formed parts moving through the guide tube do not cause clouding of the guide tube, for example, due to abrasion or damage to the guide tube. Irradiation of the guide tube by the radiation device and the resulting increased temperature causes negligible deformation or negligible damage to the guide tube.

Preferably, the guide tube has an inner diameter and the cylindrical metal formed parts each have an outer diameter. The outer diameter of the cylindrical metal formed parts is smaller than the inner diameter of the guide tube. The difference between the inner diameter of the guide tube and the outer diameter of the metal formed parts is between 1 mm and 6 mm, preferably between 2 mm and 5 mm, more preferably between 2.3 mm and 4.8 mm. The described differences between the inner diameter of the guide tube and the outer diameter of the metal formed parts enable the metal formed parts to be moved through the guide tube without tilting or jamming. At the same time, the described differences allow a constant position of the metal formed parts relative to the inspection apparatus while moving through the guide tube. Preferably, the inner diameter of the guide tube forms a cavity along the length of the guide tube through which the metal formed parts are guided.

According to an embodiment, the guide tube extends along a longitudinal axis through the inspection apparatus. This avoids obstacles that would arise, for example, due to a curved course of the guide tube. Unhindered movement of the metal formed parts through the guide tube is thus ensured.

According to another embodiment, the inspection apparatus has a receiving portion for the guide tube. The inspection apparatus is designed in such a way that the guide tube can be removed from the receiving portion and can be replaced. This means that the guide tube can be easily removed from the inspection apparatus and replaced, for example in the event of damage. Preferably, the inspection apparatus has a mechanism for manually opening the inspection apparatus. By actuating the mechanism, the inspection apparatus can be opened, allowing free access to the receiving portion through the guide tube. Preferably, the guide tube can be manually removed from the receiving portion.

Preferably, the guide tube has an outer diameter. Optionally, the outer diameter of the guide tube is in a range from 20 mm to 50 mm.

The receiving portion is designed to receive guide tubes with different outside diameters. Optionally, the inspection apparatus can inspect metal formed parts of different outer diameters. For this purpose, it is necessary to use different guide tubes whose inner diameter is matched to the corresponding outer diameter of the metal formed part to be inspected. To ensure sufficient strength of the guide tubes with different inside diameters, the guide tubes have different outside diameters. By allowing the receiving portion to accommodate guide tubes with different outer diameters, a more flexible use of the inspection apparatus for differently sized metal formed parts is achieved. Preferably, the receiving portion has at least two opposing stops that are slidably mounted on the inspection apparatus relative to each other. Preferably, each stop is formed by an end face of a body, the guide tube being clampable between the end faces. Optionally, the receiving portion comprises four stops, each two opposing stops forming a pair and the two pairs being spaced apart along the longitudinal axis of the guide tube. The two pairs are arranged, for example, outside a housing of the inspection apparatus along the longitudinal axis of the guide tube before and after the housing of the inspection apparatus.

According to an embodiment, the guide tube has a wall thickness of 2 mm to 4 mm. Preferably, the guide tube has a wall thickness of 2 mm to 3 mm with an outer diameter of the metal formed parts to be inspected between 14 mm and 17 mm. Also preferably, the guide tube has a wall thickness of 3 mm to 4 mm with an outer diameter of the metal formed parts to be inspected of 25 mm to 33 mm. Preferably, the transmittance of the guide tube is between 80% and 95% for radiation in a wavelength range of 400 nm to 800 nm with a wall thickness of the guide tube of 2 mm to 4 mm. Thus, when using different wall thicknesses, an approximately constant transmission of the radiation of the radiation device as well as of the reflection radiation through the guide tube is ensured. When using different wall thicknesses, an approximately constant amount of reflection radiation hits the sensor device, so that a reliable detection of defects by the evaluation device is possible.

Preferably, the guide tube is arranged in such a way that the metal formed parts move through the guide tube by means of gravity. Optionally, the guide tube is inclined relative to the ground so that there is a slope along the guide tube. Preferably, the metal formed parts to be inspected are fed to an upper end of the guide tube by a conveyor belt and fall through the guide tube by gravity. This means that no additional supporting measures are required for moving the metal formed parts to be inspected within the guide tube.

According to an embodiment of the invention, the guide tube can be pressurized with compressed air and is designed in such a way that the metal formed parts are moved through the guide tube by means of compressed air impacts. If, for example, the inspection apparatus is arranged in such a way that the guide tube is positioned, for example, horizontally or approximately horizontally, the metal formed parts to be inspected can be moved through the guide tube with individual blasts of compressed air. This means that the inspection apparatus can also be used in places where an inclined position of the guide tube is not possible.

According to a further embodiment of the invention, the metal formed parts are stainless steel cups, in particular battery cups. Battery cups are preferably made of steel, in particular stainless steel, and have a substantially cylindrical shape.

The above-mentioned object is also achieved by a production line comprising the features of claim 12.

According to the invention, the production line for manufacturing cylindrical metal formed parts comprises a deep-drawing press for deep-drawing the metal formed parts from blanks in multiple deep-drawing steps by means of a punch and a die. The production line further comprises a washing station for cleaning the deep-drawn metal formed parts and an inspection apparatus described above for inspecting the cleaned metal formed parts. By means of the inspection apparatus, it is possible to continuously inspect deep-drawn and cleaned metal formed parts. Preferably, the inspection apparatus is designed to inspect up to 400 metal formed parts per minute. Optionally, the cycle rate at which the metal formed parts are fed through the inspection apparatus is determined by the cycle rate of the washing station, i.e. how many metal formed parts leave the washing station per minute.

The above-mentioned object is also achieved by a method for inspecting cylindrical metal formed parts. According to the invention, the method comprises the following steps:
Providing an inspection apparatus according to the invention;
Inserting a metal formed part into the guide tube so that it is guided in the guide tube (11) through the inspection apparatus (9);
Emitting radiation so that it impinges on the metal formed part (2) and is at least partially reflected by it as reflection radiation;
Receiving the reflection radiation and converting it to image data;
Evaluating the image data and assessing whether the metal formed part (2) has production-related defects.

BRIEF DESCRIPTION OF THE DRAWINGS

The invention is described below with reference to an exemplary embodiment illustrated in the figures, in which.

DETAILED DESCRIPTION

Figure 1:
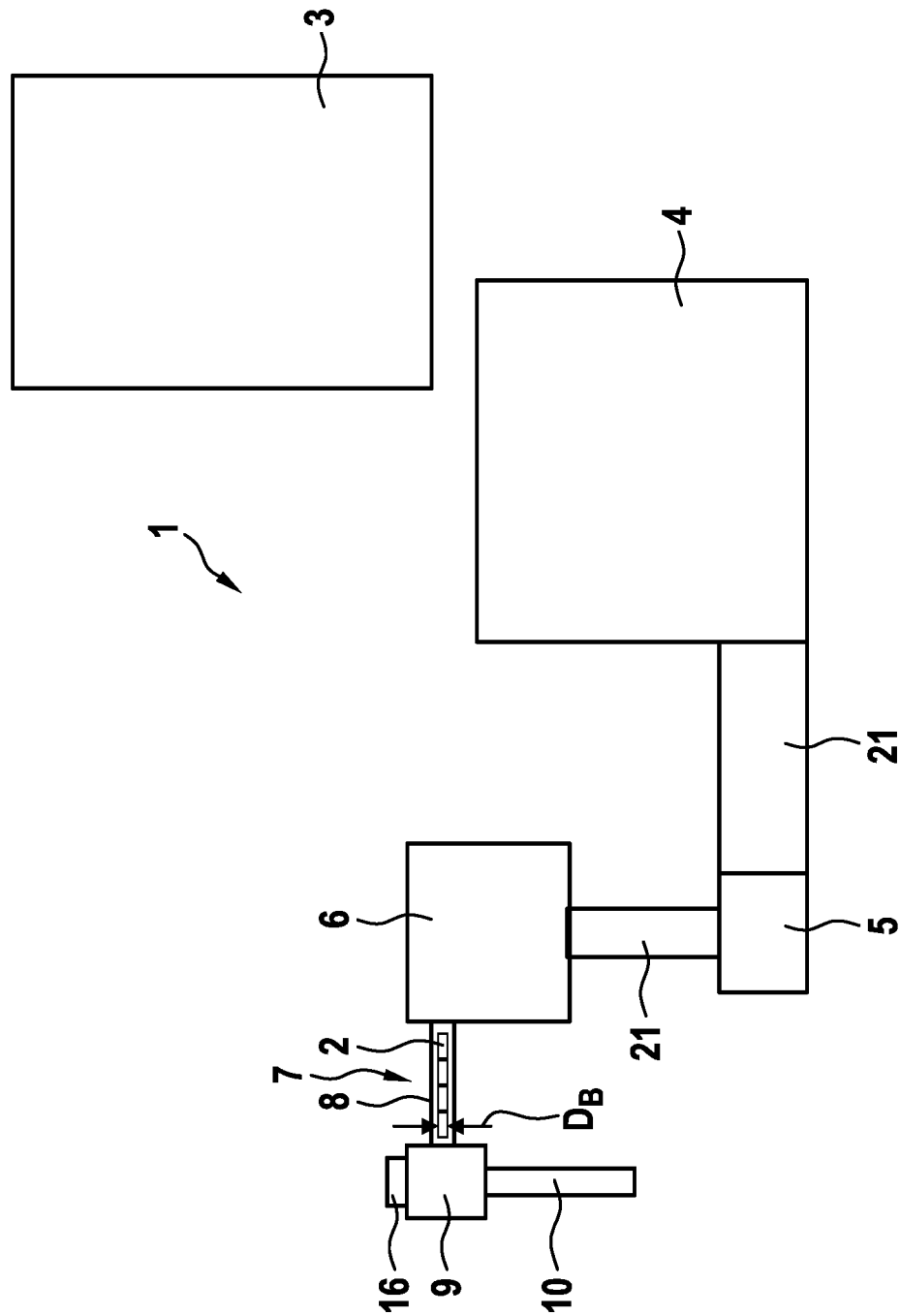
FIG. 1 shows a schematic representation of a production line with an inspection apparatus according to the invention.

FIG. 1 shows a production line 1 for manufacturing cylindrical metal formed parts in the form of battery cups 2. The production line 1 comprises a deep-drawing press 3 for deep-drawing the battery cups 2 from a blank, i.e. a round sheet blank, in multiple deep-drawing steps by means of a punch and a die. Optionally, the deep drawing press 3 can be preceded by a first station in which a cup is drawn from the blank. The cup is then deep-drawn in multiple deep-drawing steps in the deep-drawing press 3 by means of a punch in a die to form the battery cup 2.

The production line 1 further comprises a washing station 4 for cleaning the deep-drawn battery cups 2. The deep-drawing press 3 is arranged at a distance from the washing station 4. Battery cups 2 ejected from the deep-drawing press 3 are transported manually, for example in boxes or cardboard boxes, to the washing station 4.

The production line 1 further comprises a separation device 6 in the form of a centrifugal conveyor. The separation device 6 is designed to separate the washed battery cups 2 and feed them to a feed system 7. An intermediate buffer 5 in the form of a bunker is arranged between the washing station 4 and the separation device 6, which buffer is connected to the washing station 4 and the separation device 6 via a respective conveyor device 21, for example a roller conveyor or a lugged goods conveyor.

The feed system 7 has one or more conveyor belts 8, by means of which the battery cups 2 are fed to an inspection apparatus 9 for inspecting the cleaned battery cups 2. The feeding system 7 is designed to check the orientation of the battery cups 2 exiting the separation device 6 and to reject incorrectly oriented battery cups 2.

Adjacent to the inspection apparatus 9 is a roller conveyor 10. The roller conveyor 10 is designed to transport pallets with cardboard boxes located thereon. The inspected and approved battery cups 2 which exit the inspection apparatus 9 are arranged in the cardboard boxes.

Also adjacent to the inspection apparatus 9 is a container 16 for receiving defective battery cups 2. The defective battery cups 2 are not collected in the cardboard boxes on the roller conveyor 10, but are automatically separated from the other battery cups 2 beforehand via a mechanical diverter and collected in the container 16.

Figure 2:
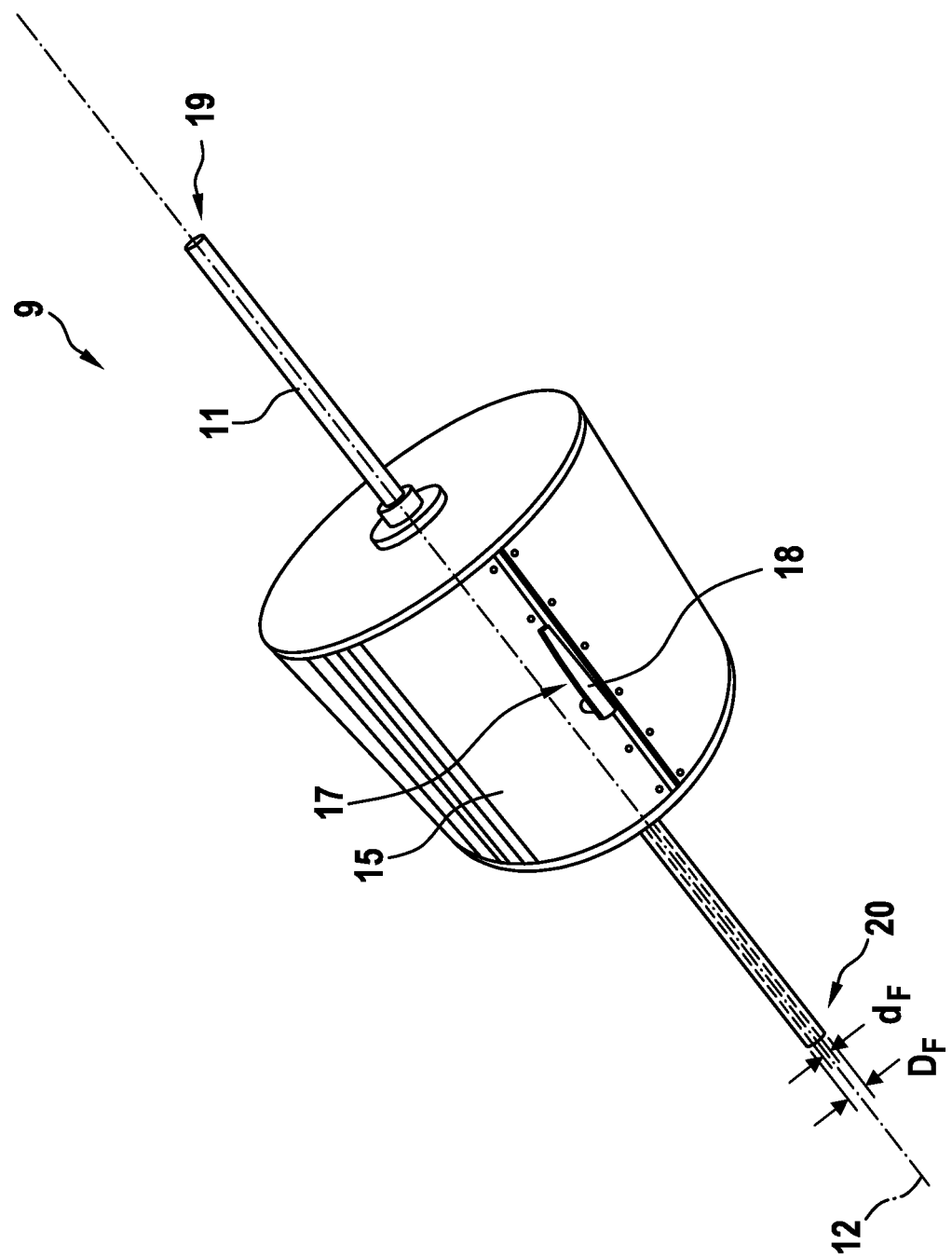
FIG. 2 shows a schematic representation of the inspection apparatus according to the invention and
FIG. 3 shows a detailed view of the inspection apparatus of FIG. 2.
Figure 3:
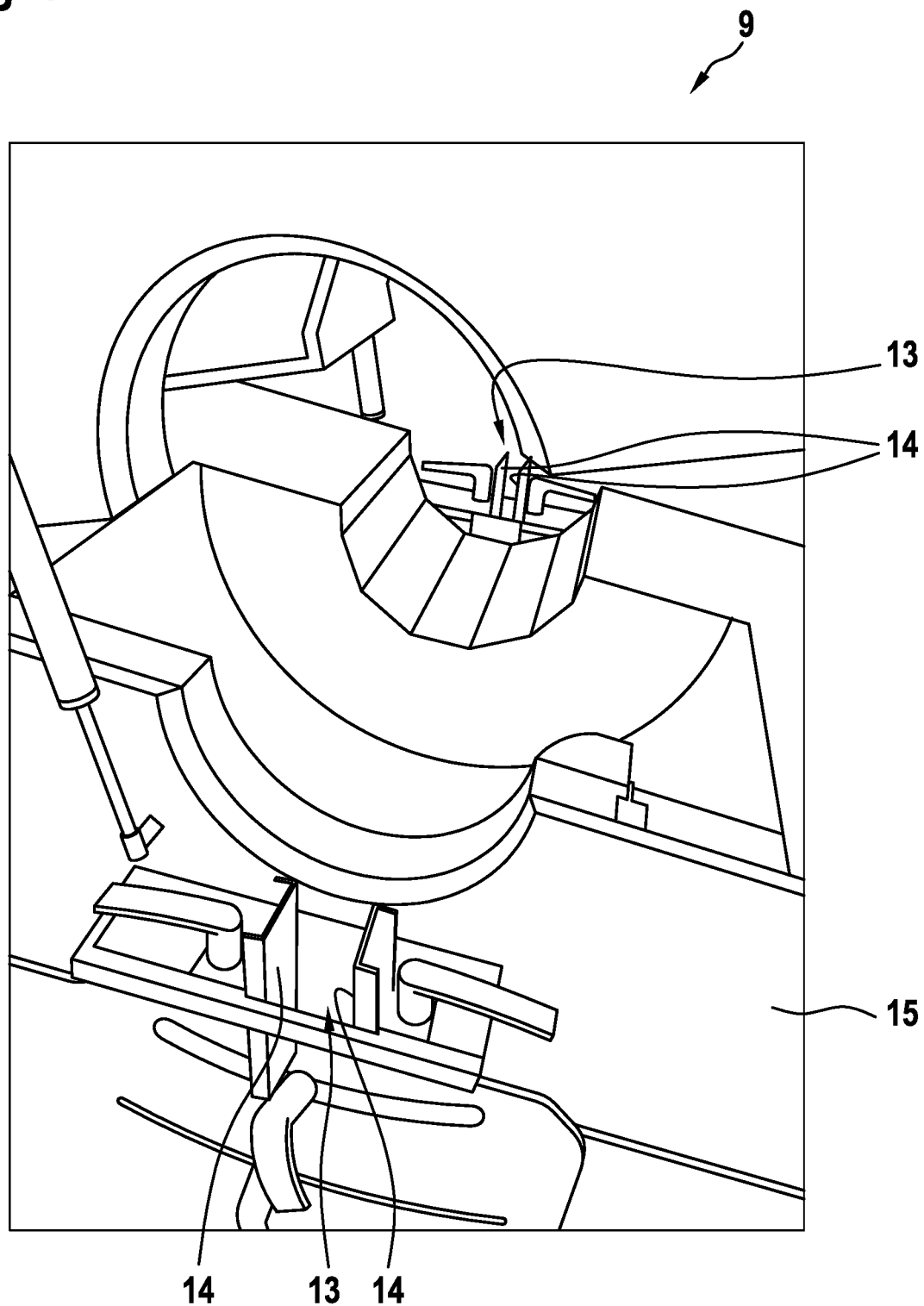

FIGS. 2 and 3 show the inspection apparatus 9 in detail. The inspection apparatus 9 comprises a guide formed as a guide tube 11. The guide tube is configured to receive the battery cups 2 to be inspected so that they are guided in the guide tube 11 through the inspection apparatus 9. The guide tube 11 has a first end 19, upper end in FIG. 2, for receiving the battery cups 2 and a second end 20, lower end in FIG. 2, at which the battery cups 2 exit the guide tube 11.

The inspection apparatus 9 further comprises a radiation device (not shown) configured to emit radiation in the direction of the guided battery cups 2, such that the radiation impinges on each of the battery cups 2 and is at least partially reflected therefrom as reflection radiation. Optionally, the radiation emitted by the radiation device is visible light having a wavelength in the range of 400 nm to 800 nm.

The inspection apparatus 9 also comprises a sensor device (not shown) which is designed to receive the reflection radiation and convert it into image data. Optionally, the sensor device is a camera device with one or more camera systems.

The inspection apparatus 9 comprises an evaluation device (not shown) which is designed to assess, based on an evaluation of the image data, whether the respective battery cup 2 has production-related defects such as parabolic cracks, holes or other damage. Optionally, the image evaluation is computer-aided by means of appropriate software.

The guide tube 11 is made of an alkaline-earth free borosilicate glass (borosilicate glass 3.3 according to DIN ISO 3585). Preferably, the guide tube 11 is made of borosilicate glass 3.3 with the trade name Duran® from the company Schott AG. The guide tube 11 has a transmittance for radiation of 80% to 95%, measured at a wall thickness of the guide tube of 2 mm and for radiation from a wavelength range of 400 nm to 800 nm. The guide tube 11 has an average coefficient of linear thermal expansion according to ISO 7991 of no more than $5 \times 10^{-6}$/K.

The guide tube 11 has an inner diameter $d_F$ and an outer diameter $D_F$ and the cylindrical battery cups 2 each have an outer diameter $D_B$ (see FIGS. 1 and 2). The inner diameter $d_F$ of the guide tube 11 forms a cavity along the length of the guide tube 11 through which the battery cups 2 are guided. The outer diameter $D_B$ of the battery cups 2 is smaller than the inner diameter $d_F$ of the guide tube 11. The difference between the inner diameter $d_F$ of the guide tube 11 and the outer diameter $D_B$ of the battery cups 2 is between 2.3 mm and 4.8 mm. The guide tube 11 has a wall thickness of 2 to 4 mm.

The guide tube 11 extends along a longitudinal axis 12 through the inspection apparatus 9. The guide tube 11 is arranged such that the battery cups 2 move through the guide tube 11 by means of gravity. For this purpose, the guide tube is tilted, i.e. arranged at an angle to the bottom contact surface of the inspection apparatus 9. Alternatively, it is equally possible to position the guide tube 1 horizontally or approximately horizontally. In this case, the guide tube 11 is pressurized with compressed air. It is designed in such a way that the battery cups 2 can be moved through the guide tube 11 by means of compressed air blasts or by means of a continuous air flow.

The inspection apparatus 9 has a receiving portion 13 for the guide tube 11. The receiving portion 13 is designed to receive guide tubes 11 with different outer diameters. The receiving portion 13 comprises four stops 14, wherein in each case two of the stops 14 are arranged opposite one another and in each case two stops 14 form a pair. The two stops 14 of a pair are arranged so as to be displaceable relative to one another and lockable at different distances from one another on the inspection apparatus 9. The two pairs being spaced apart from each other along the longitudinal axis 12 of the guide tube 11. The two pairs are arranged outside a housing 15 of the inspection apparatus 9 along the longitudinal axis 12 of the guide tube 11 before and after the housing 15 of the inspection apparatus 9.

The inspection apparatus 9 is designed in such a way that the guide tube 11 can be removed from the receiving portion 13 and replaced. For this purpose, the inspection apparatus 9 has a manually operable mechanism 17 with a rotatable handle 18. By turning the handle 18, the inspection apparatus 9 can be opened, as shown in FIG. 3, so that the receiving portion 13 for the guide tube 11 is accessible.

In the following, a method for inspecting cylindrical metal formed parts is described with reference to FIGS. 1 to 3.

The battery cups 2 are conveyed to the upper end 19 of the guide tube 11 of the inspection apparatus 9 via a conveyor belt 8 of the feed system 7. The conveyor system 7 ensures that the battery cups 2 always reach the guide tube 11 in the same orientation, e.g. with the bottom first in the conveying direction.

The battery cups 2 are individually inserted into the upper end 19 of the guide tube 11 so that they are guided in the guide tube 11 through the inspection apparatus 9. Preferably, the guide tube 11 is positioned at an angle to the ground so that the battery cups 2 move through the guide tube 11 by gravity. Each battery cup 2 is guided past one or more radiation devices. Each radiation device emits radiation in the form of visible light in the direction of the guided battery cup 2. The radiation impinges on the battery cup 2 and is at least partially reflected therefrom as reflection radiation. The sensor device, preferably in the form of one or more camera systems, receives the reflection radiation and converts it into image data. The image data is then evaluated by means of an evaluation device. Preferably, the evaluation is computer-aided by means of appropriate software.

Based on the evaluation of the image data, the evaluation device assesses whether the respective battery cup 2 has production-related defects such as parabolic cracks, holes or other damage. If the inspected battery cup 2 has defects, it is automatically separated from the other battery cups 2, for example via a mechanical diverter at the lower end 20 of the guide tube 11, and collected in the container 16. If the inspected battery cup 2 does not have any defects, it is placed in cardboard boxes arranged on the roller conveyor 10 adjacent to the inspection apparatus 9.

LIST OF REFERENCE SIGNS

1 Production line
2 Battery cup
3 Deep drawing press
4 Washing station
5 Intermediate buffer
6 Separation device
7 Feeding system
8 Conveyor belt
9 Inspection apparatus
10 Roller conveyor
11 Guide tube
$d_F$ Inner diameter (guide tube)
$D_F$ Outer diameter (guide tube)
$D_B$ Outer diameter (battery cup)
12 Longitudinal axis
13 Receiving portion
14 Stop (receiving portion)
15 Housing (inspection apparatus)
16 Container
17 Mechanism
18 Handle
19 First end (guide tube)
20 Second end (guide tube)
21 Conveyor

The invention claimed is:

1. An inspection apparatus for inspecting cylindrical metal formed parts (2) comprising,
   a guide for guiding the metal formed parts (2) to be inspected through the inspection apparatus (9),
   a radiation device which is adapted to emit radiation in the direction of the guided metal formed parts (2), so that the radiation impinges on each of the metal formed parts (2) and is at least partially reflected therefrom as reflection radiation,
   a sensor device adapted to receive the reflection radiation and to convert it into image data, and
   an evaluation device which is designed to assess, based on an evaluation of the image data, whether the respective metal formed part (2) has production-related defects,
   wherein:
   the guide is a guide tube (11) which is configured to receive the metal formed parts (2) to be inspected so that they are guided in the guide tube (11) through the inspection apparatus (9),
   the guide tube (11) has a transmittance for the radiation of 80% to 95%, measured at a wall thickness of the guide tube (11) of 2 mm and for radiation from a wavelength range of 400 nm to 800 nm and,
   the guide tube (11) has an average coefficient of linear thermal expansion according to ISO 7991 of at most $5 \times 10^{-6}$/K.

2. The inspection apparatus according to claim 1, wherein the guide tube (11) has a transmittance of 80% to 95%, measured at a wall thickness of the guide tube (11) of 4 mm and for radiation from a wavelength range of 400 nm to 800 nm.

3. The inspection apparatus according to any claim 1, wherein the guide tube (11) has a Knoop's hardness $HK_{0.1/20}$ according to ISO 9385 of 200 to 700.

4. The inspection apparatus according to claim 1, wherein the guide tube (11) is made of borosilicate glass.

5. The inspection apparatus according to claim 4, wherein the borosilicate glass is an alkaline-earth free borosilicate glass.

6. The inspection apparatus according to claim 1, wherein the guide tube (11) has an inner diameter ($d_F$) and the cylindrical metal formed parts each have an outer diameter ($D_B$) that is smaller than the inner diameter ($d_F$) of the guide tube, the difference between the inner diameter of the guide tube ($d_F$) and the outer diameter ($D_B$) of the metal formed parts being between 1 mm and 6 mm.

7. The inspection apparatus according to claim 1, wherein the guide tube (11) extends along a longitudinal axis (12) through the inspection apparatus (9).

8. The inspection apparatus according to claim 1, wherein the inspection apparatus (9) has a receiving portion (13) for the guide tube (11), and the inspection apparatus (9) is designed in such a way that the guide tube (11) can be removed from the receiving portion (13) and can be replaced.

9. The inspection apparatus according to claim 8, wherein the guide tube (11) has an outer diameter ($D_F$) and the receiving portion (13) is designed to receive guide tubes (11) with different outer diameters ($D_F$).

10. The inspection apparatus according to claim 1, wherein the guide tube (11) has a wall thickness of 2 mm to 4 mm.

11. The inspection apparatus according to claim 1, wherein the guide tube (11) is arranged in such a way that the metal formed parts (2) move through the guide tube (9) by means of gravity.

12. The inspection apparatus according to claim 1, wherein the guide tube (11) can be pressurized with compressed air and is designed in such a way that the metal formed parts (2) are moved through the guide tube (11) by means of compressed air impacts.

13. The inspection apparatus according to claim 1, wherein the metal formed parts are stainless steel cups.

14. A production line for manufacturing cylindrical metal formed parts (2) comprising,
a deep-drawing press (3) for deep-drawing the metal formed parts (2) from blanks in multiple deep-drawing steps by means of a punch and a die,
a washing station (4) for cleaning the deep-drawn metal formed parts (2), and the inspection apparatus (9) according to claim 1 for inspecting the cleaned metal formed parts.

15. A method for inspecting cylindrical metal formed parts (2), comprising the following steps:
providing the inspection apparatus according to claim 1;
inserting a metal formed part into the guide tube so that it is guided in the guide tube (11) through the inspection apparatus (9);
emitting radiation so that it impinges on the metal formed part (2) and is at least partially reflected therefrom as reflection radiation;
receiving the reflection radiation and converting it to image data; and
evaluating the image data and assessing whether the metal formed part (2) has production-related defects.

16. The inspection apparatus according to claim 6, wherein the difference between the inner diameter of the guide tube ($d_F$) and the outer diameter ($D_B$) of the metal formed parts is between 2 and 5 mm.

17. The inspection apparatus according to claim 16, wherein the difference between the inner diameter of the guide tube ($d_F$) and the outer diameter ($D_B$) of the metal formed parts is between 2.3 and 4.8 mm.

18. The inspection apparatus according to claim 13, wherein the metal formed parts are battery cups.

* * * * *